United States Patent
Aeby et al.

(10) Patent No.: US 7,021,935 B2
(45) Date of Patent: Apr. 4, 2006

(54) DENTAL INSTRUMENT FOR THE EXTRACTION OF AN OBJECT FROM A ROOT CANAL

(75) Inventors: Francois Aeby, Montagny-pres-Yverdon (CH); Gilbert Rota, Vaux et Chantegru (CH)

(73) Assignee: Maillefer Instruments Holding S.A.R.L., Ballaigues (CH)

( * ) Notice: Subject to any disclaimer, the term of this patent is extended or adjusted under 35 U.S.C. 154(b) by 70 days.

(21) Appl. No.: 10/736,422

(22) Filed: Dec. 15, 2003

(65) Prior Publication Data

US 2004/0142302 A1    Jul. 22, 2004

(51) Int. Cl.
*A61C 3/02* (2006.01)
(52) U.S. Cl. .................... 433/224; 433/165
(58) Field of Classification Search ............... 433/165, 433/224, 215
See application file for complete search history.

(56) References Cited

U.S. PATENT DOCUMENTS

| | | | | |
|---|---|---|---|---|
| 3,322,124 A | * | 5/1967 | Ireland | 433/141 |
| 4,247,285 A | * | 1/1981 | Roig-Greene | 433/141 |
| 4,337,038 A | * | 6/1982 | Saito et al. | 433/32 |
| 4,746,292 A | * | 5/1988 | Johnson | 433/141 |
| 5,085,586 A | * | 2/1992 | Johnson | 433/224 |
| 5,173,049 A | * | 12/1992 | Levy | 433/215 |
| 5,275,563 A | * | 1/1994 | Cohen et al. | 433/224 |
| 5,879,160 A | * | 3/1999 | Ruddle | 433/141 |
| 5,951,286 A | * | 9/1999 | Rhodes | 433/165 |
| 6,227,855 B1 | * | 5/2001 | Hickok et al. | 433/141 |
| 6,280,197 B1 | * | 8/2001 | Benado | 433/224 |

FOREIGN PATENT DOCUMENTS

| | | |
|---|---|---|
| BR | PI 0005652-9 A | 6/2002 |
| DE | 100 23 195 | 5/2000 |
| FR | 1213369 | 10/1959 |

OTHER PUBLICATIONS

Journal of Endodontics 1998 vol. 24 No. 6 Clinical Aid—A New Method for Retrieving Silver Points and Separated Instruments from Root Canals.

* cited by examiner

*Primary Examiner*—Ralph A. Lewis
(74) *Attorney, Agent, or Firm*—James B. Bieber; Douglas J. Hura; Daniel W. Sullivan

(57) ABSTRACT

A dental instrument for the extraction of an object from a root canal, comprising a shaft (1) having an open-end part (3) designed to receive at least a part of object (9), this open-end part (3) able to be deformed to permit seizing object (9) by clamping and then extracting it from the root canal, is characterized in that open-end part (3) is tubular and is able to plastically deform, in a manner that involves a reduction of its inner section, under the effect of a given stress.

16 Claims, 7 Drawing Sheets

Figure 1A:
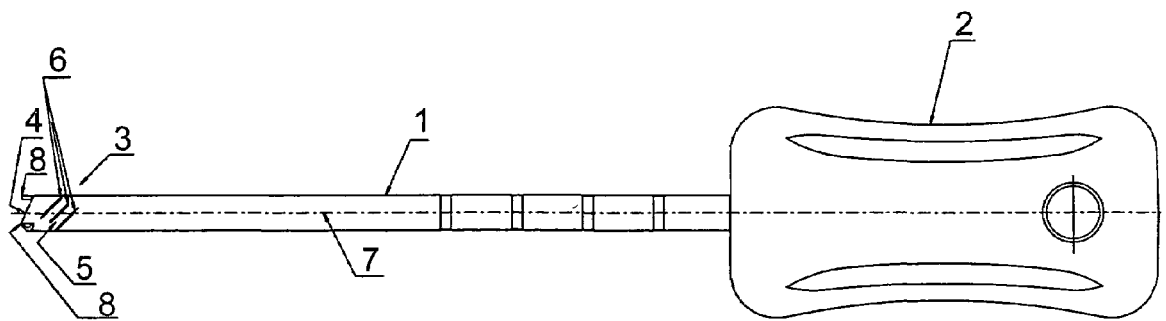

Fig.2A
Fig.2B
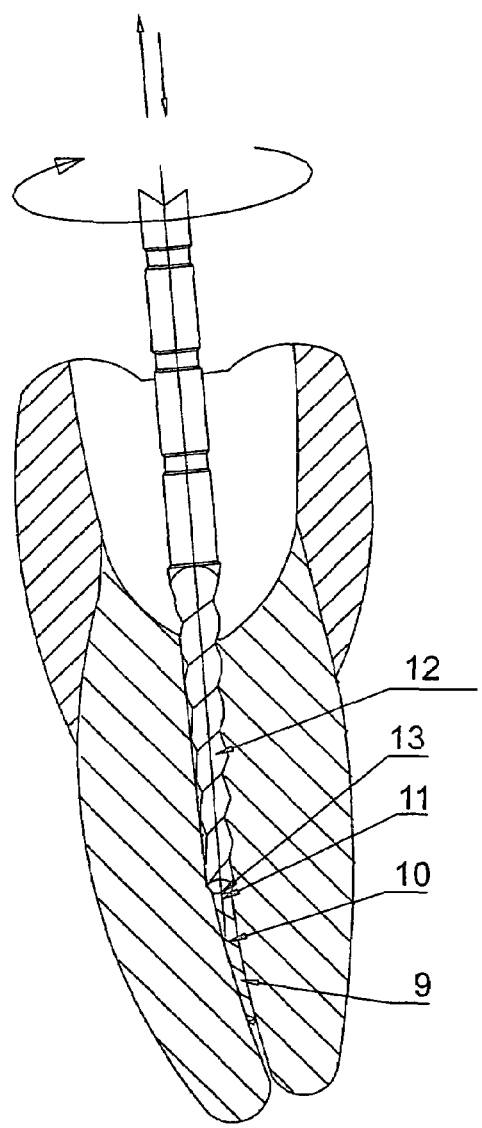
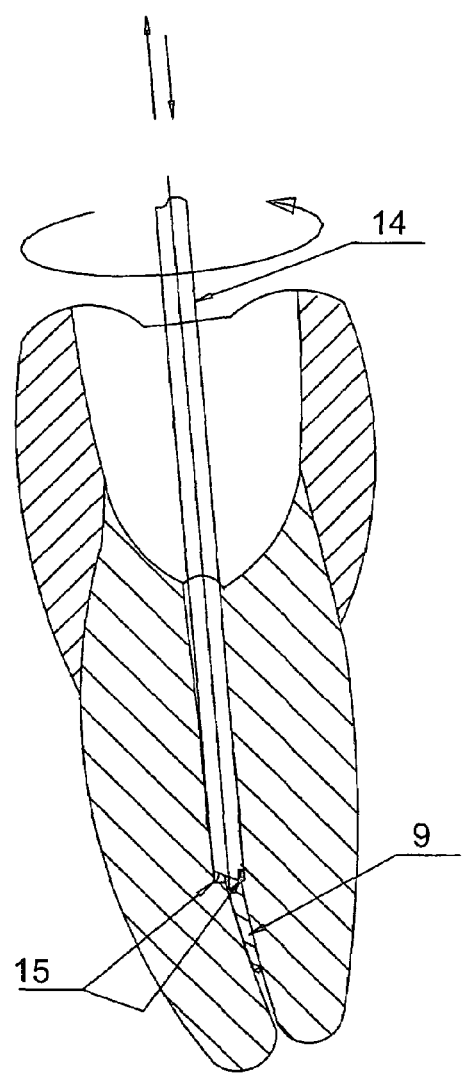

Fig.2C
Fig.2D
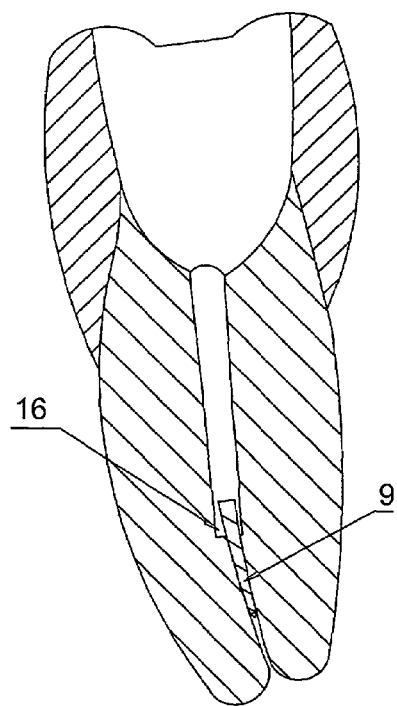
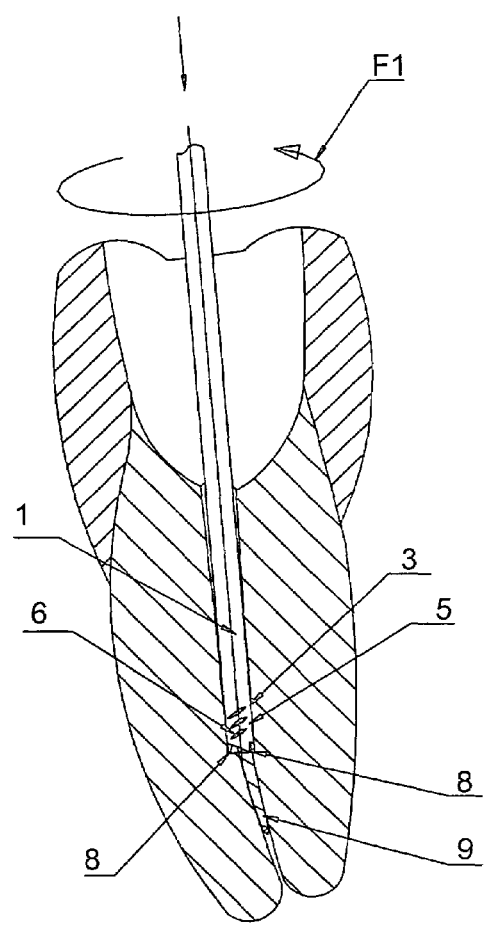

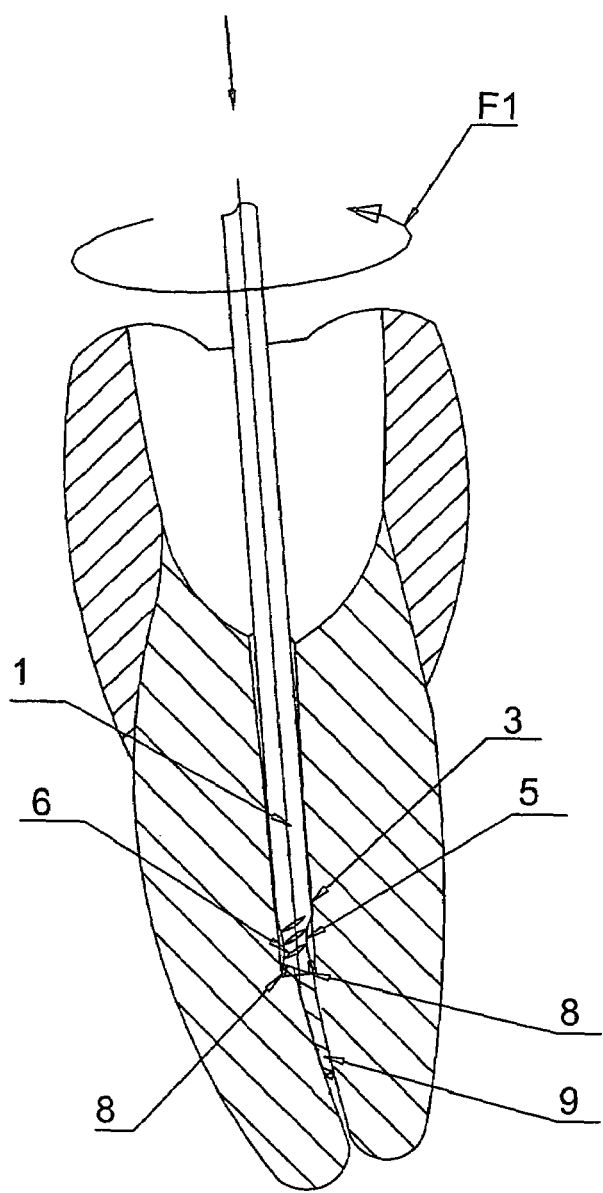
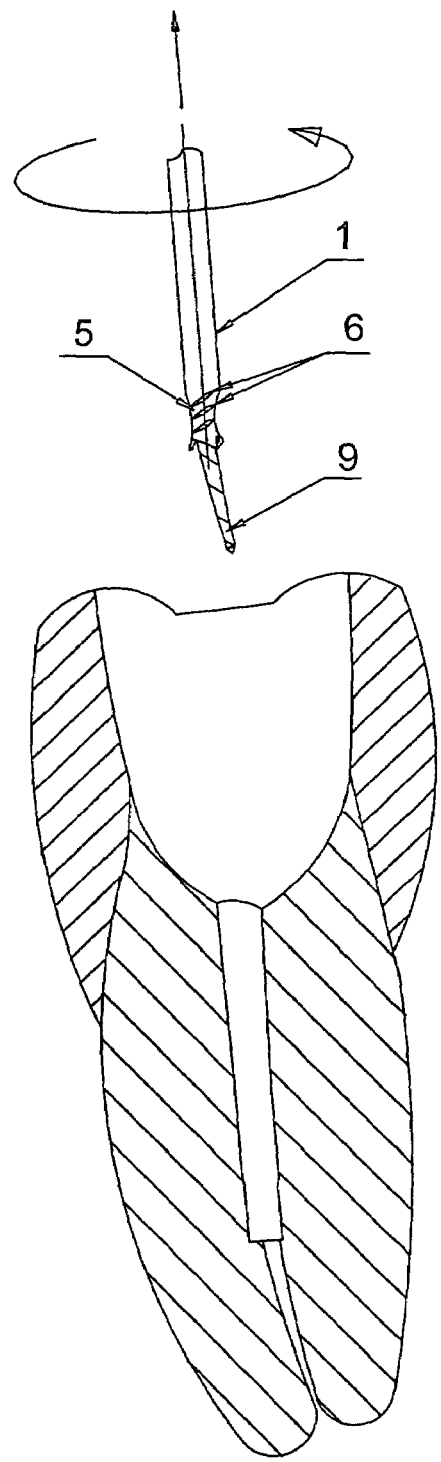

DENTAL INSTRUMENT FOR THE EXTRACTION OF AN OBJECT FROM A ROOT CANAL

The present invention concerns a dental instrument for the extraction of an object, notably a broken dental instrument, from a root canal.

Root canal treatments, called endodontic treatments, are conducted more and more frequently by a mechanized instrument. For several years, dentists made use of a series of manual files, preferably of stainless steel, that they used by alternating rotating movements with axial movements. Today, the tendency is to use a succession of nickel-titanium rotating files according to a defined sequence. This technique permits cleaning the root canal while respecting the trajectory of the original canal, in a minimal time and while respecting the basic principles of endodonty. The safety of use of these instruments depends greatly on the clinical case, the training of the dentist and, of course, on the conditions of use. This last point is important for the instrument manufacturer. The conditions of use are linked to the pressure exerted in the canal as well as the size, the rotational speed and the usage time of the instrument. Endodontic treatments are not always conducted in straight canals. There are cases where there is great curvature of the canal trajectory and other cases where access is difficult. Finally, some canals have calcifications. All these difficulties can induce instrument breakage. Good dental practice requires the dentist to remove these broken instruments.

Several techniques have been proposed to remove tips of broken instruments from a dental root canal. Notably from the documents G 92 03 692.9 and DE 100 23 195, extraction instruments are known, which comprise a shaft terminated by a clamp permitting seizing a broken instrument in a dental root canal. The clamp is made up of elastic arms that can be positioned and held in a position of clamping the broken instrument by a restraining system consisting of a handle that moves relative to the shaft and that, when it is moved in a given direction, exerts a pressure on the elastic arms.

Due to the presence of this restraining system, these extraction instruments are relatively complicated. They are also delicate to manipulate since the handle can hinder access into the mouth.

The present invention seeks to alleviate these disadvantages and proposes, for this purpose, a dental instrument for the extraction of an object from a root canal, comprising a shaft having an open-end part designed to receive at least a part of the object, this open-end part being able to be deformed to permit seizing the object by clamping and then extracting it from the root canal, characterized in that the open-end part is tubular and is able to plastically deform, so as to lead to a reduction of its inner section, under the effect of a given stress.

Thus in the present invention, due to the tubular shape of the open-end part and the ability of this part to plastically deform, no system for maintaining the clamped position is necessary. The plastic deformation is initiated directly by the dentist, typically by applying the given stress from the end of the instrument opposite the open-end part and in such a way that this given stress acts against a reaction force exerted by the dentin on the open-end part. The given stress is, for example, a twisting movement, exerted when the open-end part is blocked from rotating in the dentin, at least in the direction of twisting, or an axial pressure, exerted when the open-end part abuts axially in the dentin. In addition to its simplicity, it will be noted that the extraction instrument according to the invention has for an advantage the ability to exert a substantial clamping force, permitting the releasing of broken instruments wedged in the root canal, even when the open-end part has a reduced wall thickness.

Particular embodiments of the invention are defined in the attached claims 3 to 18.

Figure 1B:
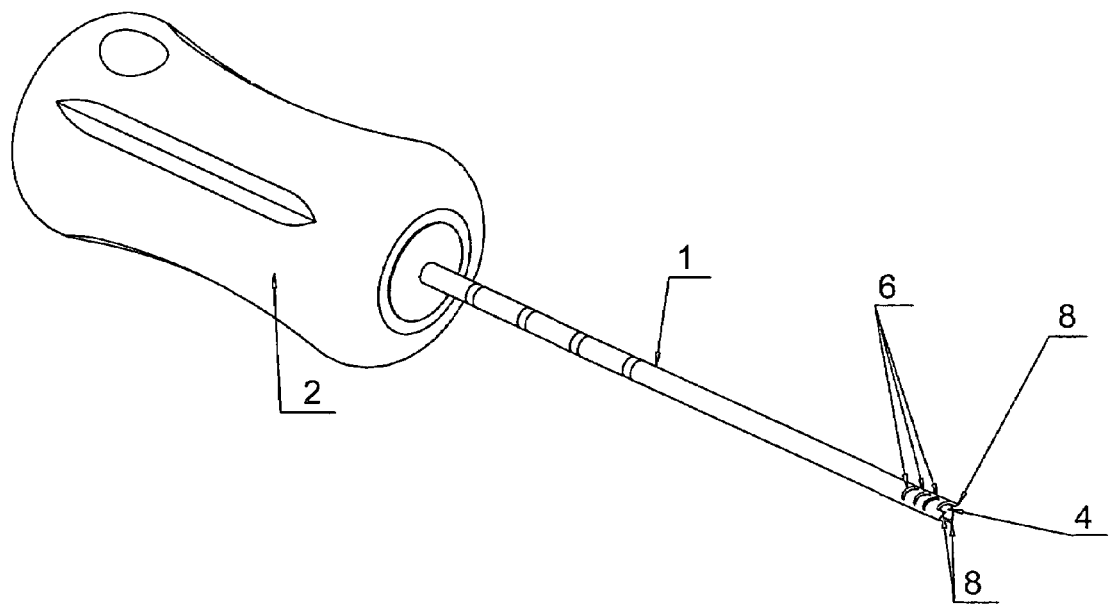

Other advantages and characteristics of the invention will appear upon reading the following detailed description made in reference to the attached drawings in which:

FIGS. 1A and 1B respectively show a profile view and a perspective view of a dental instrument according to a first embodiment of the invention;

FIGS. 2A to 2F are schematic sectional views showing an extraction process for a broken instrument from a dental root canal, using the instrument shown in FIGS. 1A and 1B; and FIGS. 3 to 15 are profile views (partially cut away in FIGS. 13 to 15) showing dental instruments according to other embodiments of the invention.

In reference to FIGS. 1A and 1B, a dental instrument for the extraction of an object, notably a broken instrument, from a root canal comprises a tubular shaft 1 and a handle 2 joined together. The distal-end part 3 of shaft 1, opposite handle 2, is open at the level of its frontal face 4 to permit passage of one end of the object to be extracted into the inside of shaft 1.

Distal-end part 3 also comprises, in proximity to its open frontal face 4, a "weakened" zone 5 having oblong, preferably traversing openings 6 on its outer surface. In the example shown, zone 5 has three series of three openings inclined 45° relative to axis 7 of shaft 1. For convenience, only one of this series of three openings has been shown. The three series are identical and distributed uniformly (at 120°) over the periphery of zone 5. These openings 6 permit distal-end part 3 to plastically deform, i.e. in a non-elastic manner, and in a manner that leads to a reduction of the inner section of zone 5, under the effect of a twist applied to shaft 1.

Distal-end part 3 also has teeth 8 on its frontal face 4, regularly distributed around the opening of this frontal face, three teeth in the example illustrated, permitting the anchoring of shaft 1 in the dentin to block the instrument from rotating during the above-mentioned twisting.

Shaft 1 is typically made of stainless steel. However, other materials, particularly metals, may be suitable, with the condition that they can undergo a permanent, non-elastic, deformation.

The wall of shaft 1 is very thin, typically 0.1 mm.

FIGS. 2A to 2F show an extraction process for a broken instrument from a dental root canal, using the instrument shown in FIGS. 1A and 1B. In the example shown, the broken instrument lodged in the root canal is a file 9 having a helical edge 10 on its outer surface.

The first step of the process consists of determining the diameter of the upper end, designated by 11, of the part of broken instrument 9 remaining in the canal by measuring the diameter of the corresponding end of the part of the broken instrument that remains outside the mouth, then to choose an extraction instrument whose inner diameter of shaft 1 is slightly superior to the diameter thus determined.

Then, as shown in FIG. 2A, the root canal is widened down to upper end 11 of the broken instrument by means of a drill 12 having a diameter roughly equal to the outer diameter of shaft 1 of the extraction instrument and whose distal end 13 is flat. FIG. 2A shows the end of this step where flat end 13 of drill 12 comes to abut against upper end 11 of the broken instrument. The space thus created in the canal will permit the extraction instrument to be guided toward the broken instrument without risk of a false route and to be centered relative to this broken instrument.

A space is then freed around upper end 11 of the broken instrument, by means of a trepan 14 having teeth 15 on its frontal face and whose diameter is roughly equal to the outer diameter of shaft 1 of the extraction instrument (FIG. 2B). FIG. 2C shows the space obtained, designated by 16, once trepan 14 is removed.

Finally, the extraction instrument penetrates into the root canal until its distal-end part 3 is lodged in space 16 and thus surrounds upper end 11 of the broken instrument (FIG. 2D). By a rapid axial movement manually impressed onto the extraction instrument by means of its handle 2, teeth 8 of shaft 1 are planted in the dentin so as to block these teeth from rotating. Then, by applying a twist to shaft 1 in the direction indicated by arrow F1, also by means of handle 2, distal-end part 3 is deformed to reduce its inner section and thus to seize upper end 11 of the broken instrument by clamping (FIG. 2E). Due to this plastic deformation, end part 3 remains in its deformed state after the application of twisting and therefore maintains its clamping force without it being necessary to provide a particular locking system. Since the broken instrument is thus seized, it can be removed by turning it in its unscrewing direction (FIG. 2F), which corresponds to the above-mentioned direction F1 of twist of shaft 1. The extraction instrument, with the broken instrument to which it remains connected, is then discarded.

In one variant of the extraction process, trepan 14 is the extraction instrument 1-2 itself, that is to say, that the extraction instrument, with its teeth 8, is used to create space 16 around upper end 11 of the broken instrument. In order to do this, one digs into the dentin by a movement of rotation and axial pressure sufficiently slow so as not to lead to deformation of distal-end part 3. Once space 16 is created, a more rapid movement is applied to the instrument in order to induce the twist and therefore the clamping of object 9 (FIG. 2E).

Figure 3:
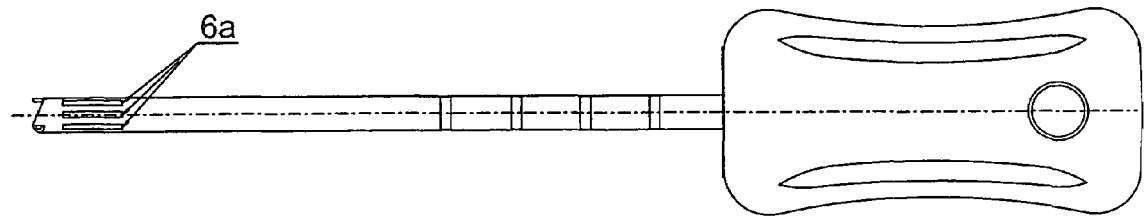
Figure 4:
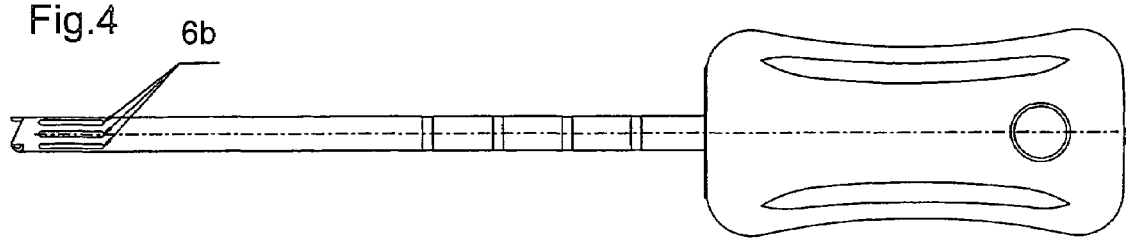
Figure 5:
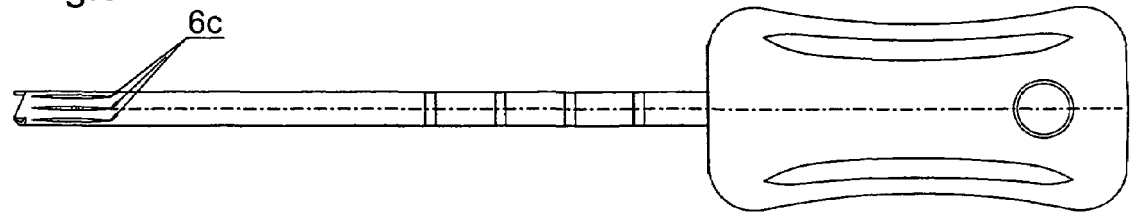
Figure 6:
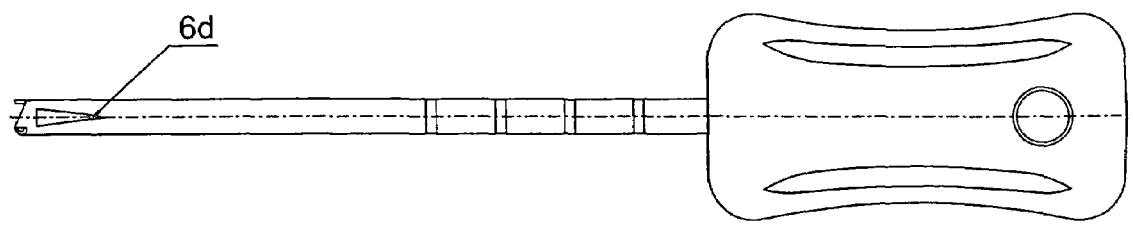
Figure 7:
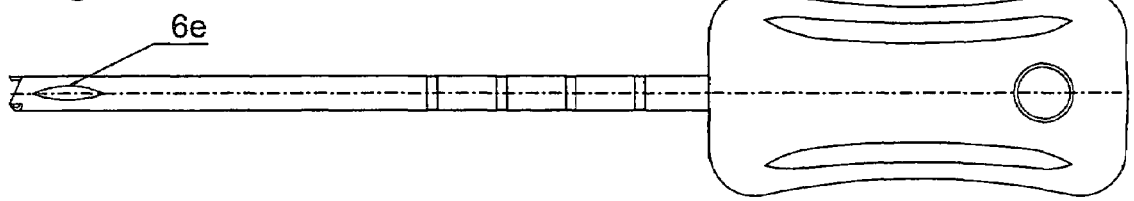
Figure 8:
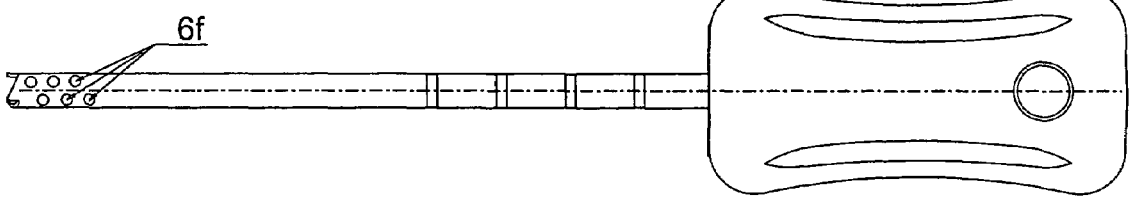
Figure 9:
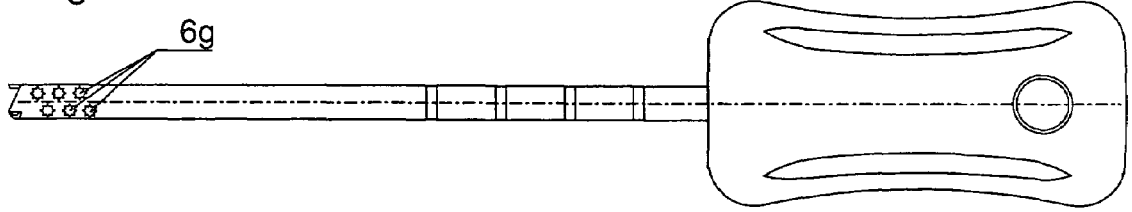
Figure 10:
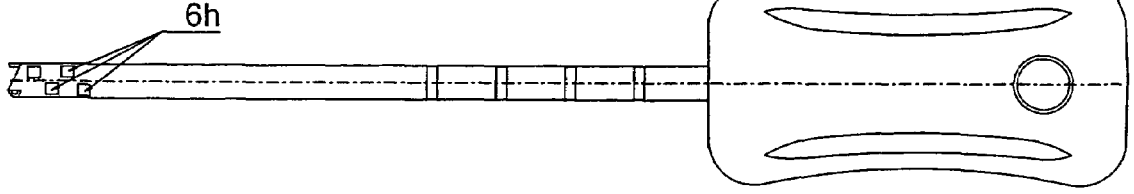

FIGS. 3 to 13 show extraction instruments according to other embodiments of the invention, able to be used in the same process as that described above. In the examples of FIGS. 3 to 7, the openings with oblong deformation are not inclined, as in the example of FIGS. 1A and 1B, but are parallel to the axis of shaft 1. These oblong openings can have different shapes, for example rectangular (FIG. 3, reference 6a), rectangular with rounded edges (FIG. 4, reference 6b), almond-shaped (FIGS. 5 and 7, references 6c and 6e) or triangular (FIG. 6, reference 6d). The number of these openings can vary and can be equal to nine, for example (three series of three openings, uniformly distributed along the periphery of the distal-end part; FIGS. 3–5) or equal to three (three openings, uniformly distributed along the periphery of the distal-end part; FIGS. 6, 7). The deformation openings can also be made up of holes of variable shape, for example, round, star-shaped or square, arranged in a staggered manner (FIGS. 8–10, references 6f–6h).

Figure 11:
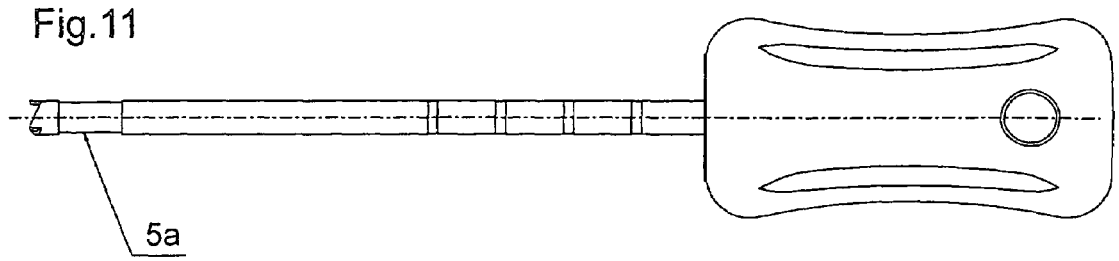

According to another variant, shown in FIG. 11, the distal-end part of the instrument shaft has a zone 5a of reduced wall thickness relative to the rest of the shaft, instead and in place of deformation openings. This zone of reduced wall thickness has the same inner diameter as the rest of the shaft. As in the preceding examples, this zone constitutes a weakened zone that, under the effect of a twist, deforms in a manner leading to a reduction of its inner section.

Figure 12:
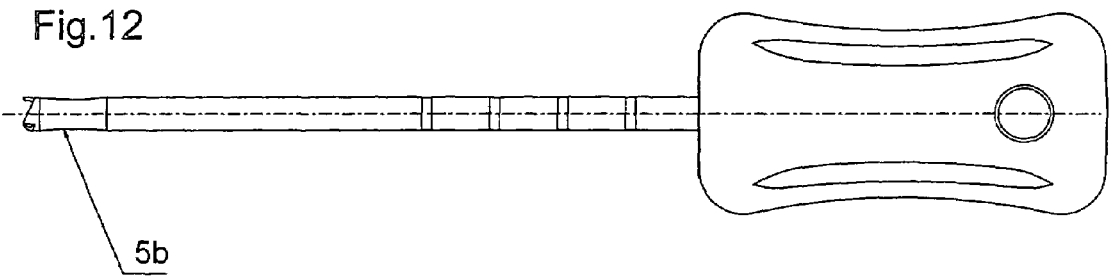

FIG. 12 illustrates an extraction instrument based on the same principle as that of FIG. 11, but in which the wall thickness of weakened zone 5b is variable and has a minimum in the central part of zone 5b.

Figure 13:
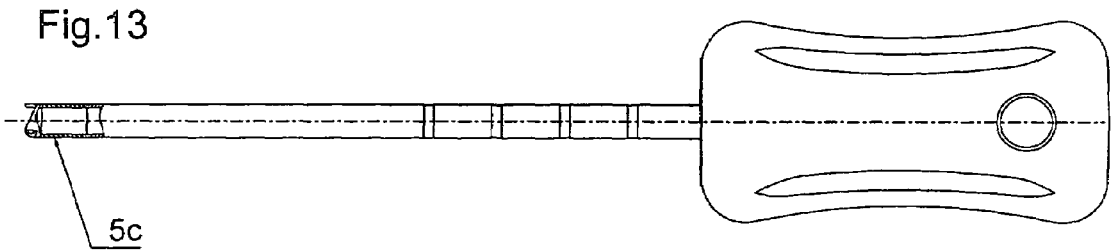

In the example of FIG. 13, weakened zone 5c has the same thickness of the wall and the same internal diameter as the rest of the shaft, but is made of a more malleable material than that of the rest of the shaft. Weakened zone 5c is, for example, made of copper and the rest of the shaft is made of stainless steel. Weakened zone 5c is attached to the rest of the shaft, for example, by soldering or brazing.

In another variant (not shown), the weakened zone is made up of a zone of the distal-end part of the shaft, which [zone] has been thermally pretreated to render it more malleable than the rest of the shaft.

Figure 14:
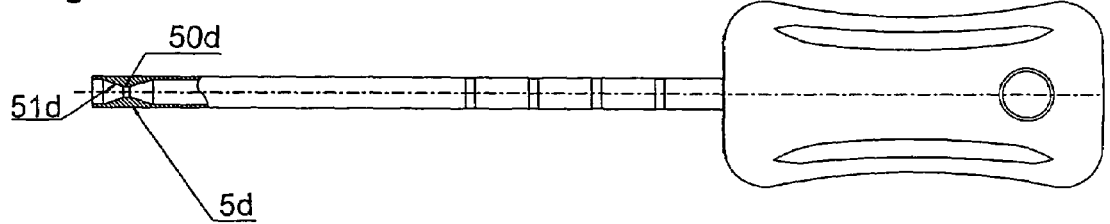

FIG. 14 shows another embodiment, in which weakened zone 5d has on its inner surface a narrowing 50d defining a cone 51d flared toward the opening of the distal-end part and whose function is to be wedged around the upper end of the broken instrument in the manner of a Morse cone. This cone 51d can thus serve as a means for blocking the distal-end part of the instrument shaft from rotating, instead and in place of teeth 8, in the case where the broken instrument is itself blocked from rotating in the canal.

Figure 15:
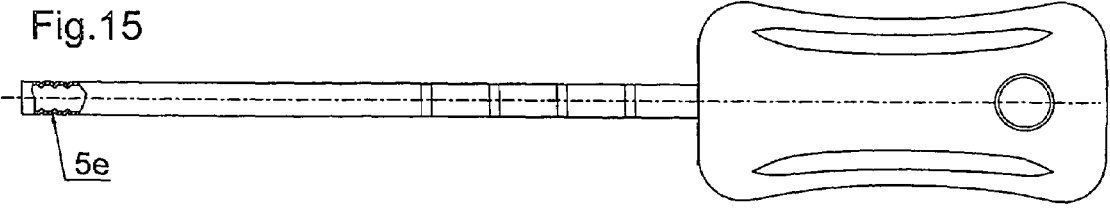

FIG. 15 shows yet another embodiment, in which, unlike all the embodiments described above, weakened zone 5e is designed to deform under the action of an axial pressure rather than a twist, exerted manually by means of the handle of the instrument when the shaft abuts axially in the space freed around the upper end of the broken instrument. For this purpose, weakened zone 5e has a zigzag-shaped wall that is compressed under the action of an axial pressure, thus reducing the inner section of the weakened zone.

The invention claimed is:

1. A dental instrument for extraction of an object from a root canal, comprising:
   a tubular shaft having an open end part of sufficient inner section to receive a portion of said object; and
   a weakened zone of said end part that is plastically deformable under a stress to reduce said inner section to clamp onto said object portion sufficiently for said extraction,
   wherein said deforming stress is a twisting motion of said shaft.

2. The dental instrument of claim 1 wherein said weakened zone comprises at least one deformation opening.

3. The dental instrument of claim 2 wherein said deformation opening is traversing.

4. The dental instrument of claim 2 wherein said weakened zone deformation openings are formed in a wall portion of the open-end part and inclined 45° relative to said shaft.

5. The dental instrument of claim 4 wherein said zone has three series of three deformation openings uniformly distributed about the periphery of said open-end part.

6. The dental instrument of claim 2 wherein said zone has deformation openings parallel to the axis of the shaft.

7. The dental instrument of claim 2 wherein said deformation openings are arranged in a staggered manner.

8. The dental instrument of claim 1 wherein said weakened zone comprises a zone of reduced wall thickness relative to the rest of the shaft, designed to undergo plastic deformation.

9. The dental instrument of claim 1 wherein said weakened zone comprises a material that is less hard than the material of which the rest of the shaft is made, designed to undergo plastic deformation.

10. The dental instrument of claim 1 wherein said weakened zone comprises a thermally pretreated zone to render it less strong than the rest of the shaft, this zone designed to undergo plastic deformation.

11. The dental instrument of claim 1 said shaft comprising a means to block said open-end part from rotating in the dentin, at least in the direction of the twist, during application of said deforming stress twisting motion.

12. The dental instrument of claim 11 wherein said blocking means comprises teeth situated on a peripheral face of said open-end part.

13. The dental instrument of claim 12 wherein said teeth can be used to dig into the dentin.

14. The dental instrument of claim 11 wherein said blocking means comprises a portion of the inner surface of the open-end part having a conical shape flared toward the opening of the open-end part so as to be able to become wedged around one end of the object.

15. The dental instrument of claim 1 further comprising a handle for twisting said shaft.

16. The dental instrument of claim 1 wherein said deforming stress further comprises an axial pressure and said weakened zone comprises a zigzag-shaped wall that collapses to clamp said object for extraction.

* * * * *